(12) United States Patent
Shanov et al.

(10) Patent No.: US 10,265,205 B2
(45) Date of Patent: Apr. 23, 2019

(54) METHODS FOR MAKING MAGNESIUM BIODEGRADABLE STENTS FOR MEDICAL IMPLANT APPLICATIONS

(71) Applicant: UNIVERSITY OF CINCINNATI, Cincinnati, OH (US)

(72) Inventors: Vesselin N. Shanov, Cincinnati, OH (US); Prabir Roy-Chaudhury, Cincinnati, OH (US); Mark J. Schulz, West Chester, OH (US); Zhangzhang Yin, Cincinnati, OH (US); Begona Campos-Naciff, Cincinnati, OH (US); Yang Wang, Mason, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 0 days.

(21) Appl. No.: 15/496,710

(22) Filed: Apr. 25, 2017

(65) Prior Publication Data
US 2017/0281377 A1  Oct. 5, 2017

Related U.S. Application Data

(62) Division of application No. 14/403,170, filed as application No. PCT/US2013/032374 on Mar. 15, 2013, now Pat. No. 9,655,752.
(Continued)

(51) Int. Cl.
*A61F 2/88* (2006.01)
*A61F 2/92* (2013.01)
(Continued)

(52) U.S. Cl.
CPC ............... *A61F 2/915* (2013.01); *A61F 2/88* (2013.01); *A61F 2/92* (2013.01); *A61F 2/958* (2013.01); *A61L 31/022* (2013.01); *A61L 31/14* (2013.01); *A61L 31/148* (2013.01); *A61L 31/16* (2013.01); *A61F 2002/91558* (2013.01);
(Continued)

(58) Field of Classification Search
CPC ...... A61F 2/915; A61F 2/07; A61F 2240/001; A61F 2002/91575; A61F 2/90; A61F 2002/91558; A61F 2210/0004; A61F 2210/0076; A61F 2230/0069; A61F 2220/0058; A61F 2/91; A61F 2002/072; A61F 2250/0067; A61F 2/92; A61F 2002/30962
See application file for complete search history.

(56) References Cited

U.S. PATENT DOCUMENTS

| | | |
|---|---|---|
| 5,391,142 A | 2/1995 | Sites et al. |
| 5,556,413 A * | 9/1996 | Lam .......................... A61F 2/88 606/198 |

(Continued)

OTHER PUBLICATIONS

Masuda, Elna M. et al, "Stent-Graft Arteriovenous Fistula: An Endovascular Technique in Hemodialysis Access"; J Endovasc Surg 1998; 5: 18-23.

*Primary Examiner* — Ann Schillinger
(74) *Attorney, Agent, or Firm* — Dinsmore & Shohl LLP

(57) ABSTRACT

Methods for making a magnesium biodegradable stent for medical implant applications, using magnesium foil or pure magnesium or magnesium alloys that are biodegradable and performing a lithographic technique to configure the features and dimensions of the magnesium foil, and rolling the magnesium foil to form a cylinder.

13 Claims, 18 Drawing Sheets

Related U.S. Application Data

(60) Provisional application No. 61/649,730, filed on May 21, 2012.

(51) Int. Cl.
    *A61F 2/915*     (2013.01)
    *A61L 31/02*     (2006.01)
    *A61L 31/14*     (2006.01)
    *A61L 31/16*     (2006.01)
    *A61F 2/958*     (2013.01)

(52) U.S. Cl.
    CPC ........... *A61F 2210/0004* (2013.01); *A61F 2220/0033* (2013.01); *A61F 2220/0075* (2013.01); *A61F 2240/001* (2013.01); *A61F 2250/0067* (2013.01); *A61F 2250/0081* (2013.01); *A61F 2250/0082* (2013.01); *A61L 2300/41* (2013.01); *A61L 2300/416* (2013.01)

(56) References Cited

U.S. PATENT DOCUMENTS

| | | |
|---|---|---|
| 7,074,220 B2 | 7/2006 | Hill et al. |
| 7,736,687 B2 | 6/2010 | Sims et al. |
| 7,927,529 B2 | 4/2011 | Dave |
| 7,981,258 B2 | 7/2011 | Johnson et al. |
| 2005/0149175 A1* | 7/2005 | Hunter ............... A61B 17/11 623/1.42 |
| 2005/0160891 A1 | 7/2005 | Koch |
| 2007/0032857 A1* | 2/2007 | Schmid ............... A61F 2/915 623/1.16 |
| 2008/0069858 A1* | 3/2008 | Weber ............... A61L 31/084 424/426 |
| 2010/0063580 A1 | 3/2010 | McClain et al. |
| 2010/0215708 A1 | 8/2010 | Lumbuehl et al. |
| 2011/0066223 A1 | 3/2011 | Hossainy et al. |
| 2011/0201990 A1 | 8/2011 | Franano |
| 2012/0016203 A1 | 1/2012 | King |
| 2012/0089414 A1 | 4/2012 | Jung et al. |
| 2012/0095489 A1 | 4/2012 | Rudakov |

\* cited by examiner

METHODS FOR MAKING MAGNESIUM BIODEGRADABLE STENTS FOR MEDICAL IMPLANT APPLICATIONS

CROSS REFERENCE TO RELATED APPLICATIONS

This application is a divisional of U.S. application Ser. No. 14/403,170, filed on Nov. 21, 2014, which is a § 371 of International Application No. PCT/US2013/032374, filed Mar. 15, 2013, which claims priority under 35 U.S.C. § 119(e) to U.S. Provisional Patent Application Ser. No. 61/649,730, filed on May 21, 2012, each of which is hereby incorporated by reference in its entirety.

FIELD OF THE INVENTION

This application relates to the design and use of magnesium biodegradable stents for placement in sites such as in ureters, bile ducts, and bronchi, and in applications such as promoting maturation of arteriovenous fistulas.

BACKGROUND OF THE INVENTION

Stents are devices used for inserting in a vessel or other part, employed in many cases to provide support for or prevent collapse of parts such as blood vessels. In specific cases, for example, stents are placed within arteries that have become dangerously narrow or during surgeries related to overcome blockages. Stent applications are not limited to blood vessels but include also parts such as ureters, bile ducts, and bronchi. Currently, stents are made of corrosion resistant metals such as titanium-nickel alloys and stainless steel. These stents may need in some cases to be removed, which requires a secondary intervention into the body.

Due to this problem of necessary removal, there are continuous efforts to manufacture biodegradable stents that can be absorbed in the body. This would provide significant advantages such as decreasing immune responses to non-endogenous materials and avoid a secondary, invasive procedure for removal of the stent. Polymer biodegradable stents for cardiovascular applications based on poly (D, L-lactic-co-glycolic acid) (PLGA) and poly (D, L-lactic acid) (PLA), polyglycolic acid (PGA) are known in the art. However, these stents are not equal to non-degradable metal stents in terms of mechanical properties.

Biodegradable magnesium implants attract significant attention because of certain advantages they offer compared to conventional metal implants. Magnesium corrodes in the body thus allowing elimination of a second surgery to remove the implant. The main approach to controlling magnesium properties is based on doping and alloying with a variety of different elements. Lately, magnesium based biodegradable stents for temporary scaffolding of coronary arteries have been introduced.

Major efforts related to stent manufacturing are focused on engraving the stent configuration. Currently, this operation employs laser cutting of a stent tube, followed by polishing, since the laser beam evaporates material that partly deposits on the surface of the stent. This approach is expensive and the productivity is low. The latter is related to the scanning speed of the laser that processes the stents one by one. Another approach is braiding of wire made of the stent material. Braiding has some advantages for making of magnesium stents that helps in overcoming the low elasticity of this metal. This approach requires a great amount of thin magnesium wire with a diameter of a couple hundred microns to be fed into the braiding machine. Currently, magnesium wire is available on the market from only a few vendors offering limited diameters and at very high prices. In addition, the low tensile strength of the magnesium wire demands redesigning of the available micro-braiders and modifying their mechanics in a way that they do not break the wire during braiding.

Methods of making and using biodegradable magnesium stents are herein described that overcome the long-felt needs of high-quality, reliable biodegradable stents and overcome specific problems described above.

SUMMARY

Specific embodiments herein describe methods for making a magnesium biodegradable stents for medical implant applications comprising providing magnesium foil comprising pure magnesium or magnesium alloys that are biodegradable, performing a lithographic technique to configure the features and dimensions of the magnesium foil wherein the lithographic technique is used to transfer the stent features to both sides of the magnesium foil, wherein the lithographic technique is selected from at least one of optical photolithography, electron beam lithography, x-ray lithography, and nanoimprint lithography, or a combination of these techniques; etching the magnesium foil; and rolling the magnesium foil to form a cylinder.

Specific embodiments herein describe magnesium biodegradable stents for medical implant applications comprising a cylinder comprising magnesium foil comprising pure magnesium or magnesium alloys that are biodegradable, wherein the cylinder is configured to be balloon-expandable, and the cylinder has a longitudinal gap between the two edges along a longitudinal length of the cylinder, and the cylinder is configured such that the two edges along the longitudinal length overlap each other such that a spiral is formed as seen from a side view looking down the longitudinal length of the stent.

Yet more specific embodiments here describe magnesium biodegradable stents for medical implant applications comprising a cylinder comprising magnesium foil comprising pure magnesium or magnesium alloys that are biodegradable, wherein the cylinder is configured to be balloon-expandable, has an upper and a lower ring, the rings being at each end along the longitudinal length of the cylinder, and wherein the upper and lower rings are discontinuous and have no longitudinal sections of a welded seam between circumferential struts on the stent, such that the stent is stress-free with regards to longitudinal contraction of the stent and such that bending of the stent is prevented and overstressing or breaking of meandering wire connections between the struts is also prevented when the stent is expanded.

Even more specific embodiments here describe methods for placement of a magnesium biodegradable stent for medical implantations comprising providing a stent comprising a magnesium biodegradable stent for medical implant applications comprising a cylinder comprising magnesium foil comprising pure magnesium or magnesium alloys that are biodegradable, wherein the cylinder is configured to be balloon-expandable, and the cylinder has a longitudinal gap between the two edges along a longitudinal length of the cylinder, and the cylinder is configured such that the two edges along the longitudinal length overlap each other such that a spiral is formed as seen from a side view looking down the longitudinal length of the stent; anesthetizing a patient; surgically prepping the patient, giving pre-emptive analgesics to the patient; incising the site of surgery as appropriate for subsequent arteriovenous placement; creating an arteriovenous fistulae with an end to side anastomosis between an artery and a vein; crimping the stent; inserting the stent into the vein; positioning the stent so a first end of the stent is aligned with an open end of the dissected vein; suturing the vein to the artery; incising the artery across the anastomosis; inserting a balloon via the incision in the artery to the stent; expanding the balloon to expand the stent; and suturing the incision in the artery.

Yet more specific embodiments here describe methods for placement of magnesium biodegradable stents for implantation in a surgically-created arteriovenous fistulae comprising providing a stent comprising a magnesium biodegradable stent for medical implant applications comprising a cylinder comprising magnesium foil comprising pure magnesium or magnesium alloys that are biodegradable, wherein the cylinder is configured to be balloon-expandable, has an upper and a lower ring, the rings being at each end along the longitudinal length of the cylinder, and wherein the upper and lower rings are discontinuous and have no longitudinal sections of a welded seam between circumferential struts on the stent, such that the stent is stress-free with regards to longitudinal contraction of the stent and such that bending of the stent is prevented and overstressing or breaking of meandering wire connections between the struts is also prevented when the stent is expanded; and also a design that can protect as needed the entire region of surgical injury and also have the ability to self expand if the AVF expands really well so that the stent will never be a hindrance to full outward expansion; creating an arteriovenous fistulae with an end to side anastomosis between an artery and a vein; inserting the stent into the vein using a sleeve over the stent as needed and crimping the stent as needed; positioning the stent so a first end of the stent is aligned with an open end of the dissected vein; suturing the vein to the artery; incising the artery across the anastomosis; inserting a balloon via the incision in the artery to the stent; expanding the balloon to expand the stent; and suturing the incision in the artery; or alternatively placing the stent under direct vision into the cut end of the vein with or without a sleeve and/or crimping device, performing the anastomosis and then dilating the stent through a venous approach. Alternatively, the stent can be configured so that it extends into the artery as needed and covers the entire peri-anastomotic area; with the stent being configured/designed such that arterial flow comes in well through the gaps in the stent.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, where.

DESCRIPTION OF EMBODIMENTS

Figure 1:
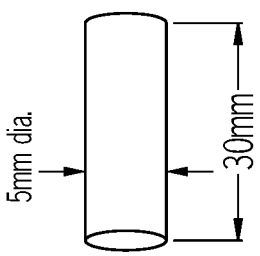
FIG. 1 illustrates specific embodiments of steps to form a magnesium stent by etching and rolling of a thin magnesium foil
Figure 1:
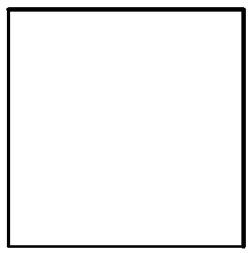
Figure 1:
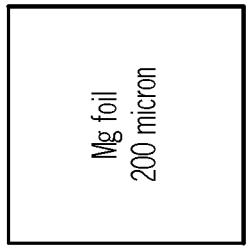

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used herein is for describing particular embodiments only and is not intended to be limiting of the invention. As used in the specification and appended claims, the singular forms "a," "an," and "the"

are intended to include the plural forms as well, unless the context clearly indicates otherwise.

Unless otherwise indicated, all numbers expressing quantities of ingredients, properties conditions, and so forth as used in the specification and claims are to be understood as being modified in all instances by the term "about," which is intended to mean up to ±10% of an indicated value. Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

As used herein, the term "biodegradable" refers generally to degradation of a stent such that the stent is decayed, decomposed, or caused to deteriorate and that during such degradation toxins are not produced at a significant level.

As used herein, the term arteriovenous "maturation" refers to progression and increased functionality of the artery-venous connection developed from the time of surgery for a hemodialysis access point.

Specific embodiments illustrated herein are directed to the manufacturing of biodegradable magnesium based stents for medical applications including but not limited to scaffolding of any blood vessels (cardiovascular, arteriovenous fistula, etc.), urine ducts, bile ducts and tracheal ducts. The stent, in specific embodiments, is produced by chemical etching of magnesium foil through a mask created by using any lithographic approach including Optical photolithography, electron beam lithography, x-ray lithography, nanoimprint lithography or a combination of the techniques. The embodiments described herein may make the production of magnesium based biodegradable stents inexpensive and scalable for mass production.

Specific embodiments are directed to methods of making magnesium stents as described below. The stent has in specific embodiments been fabricated of a thin magnesium foil. Making the stent can include several steps illustrated in FIG. 1. FIG. 1 depicts steps to form a magnesium stent by etching and rolling of a thin magnesium foil.

The used material in specific embodiments can be approximately 200 microns thick of pure magnesium foil or, in additional specific embodiments, approximately 250 micrometers thick of foil made of magnesium alloy AZ31, which has been processed by photochemical etching. Other magnesium alloys can also be employed. In specific embodiments the pure magnesium can be from about 100 to about 300 microns thick and the alloy can be from about 200 to about 300 microns thick. This approach can include photolithography to transfer a feature on both sides of the foil, followed by chemical etching. The resulting, etched foil can have a desired feature that is determined by the photolithographic mask. A variety of features and configurations with different dimensions can be produced with this technique.

Figure 2:
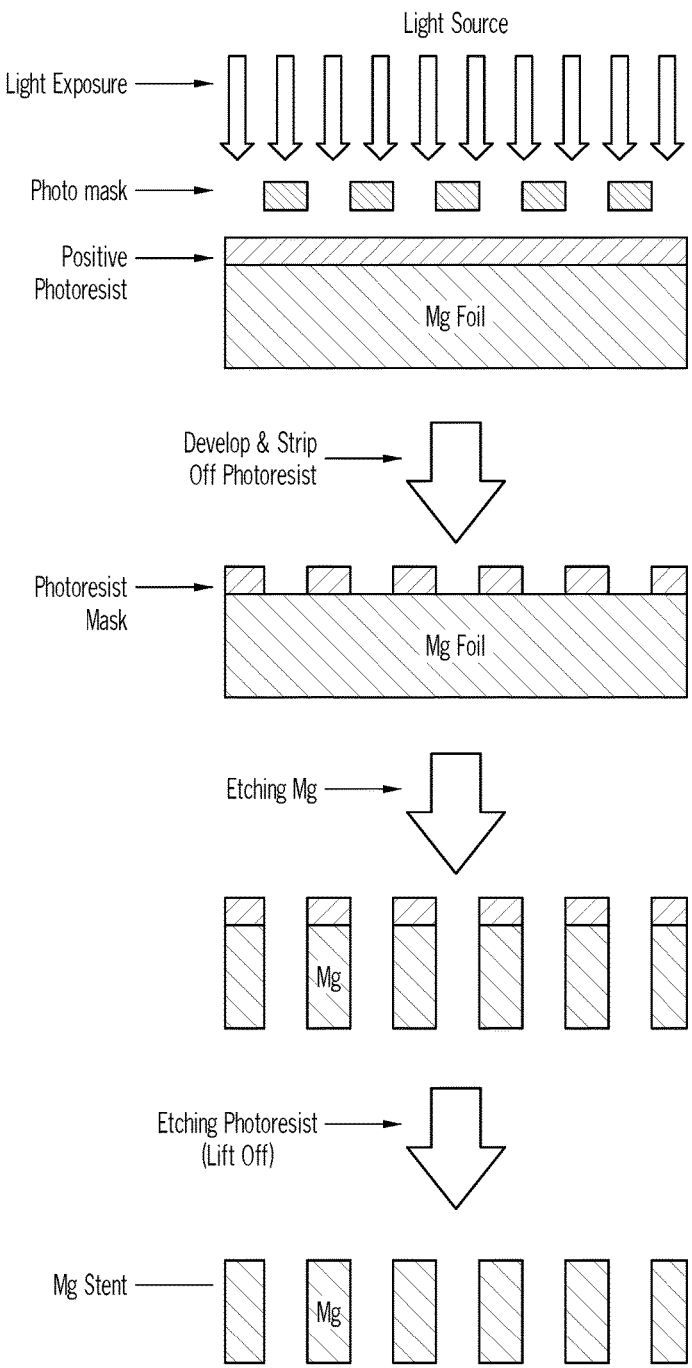
FIG. 2 illustrates specific embodiments of steps of photolithography of the present disclosure to fabricate features of the magnesium stent.

FIG. 2 illustrates the processing steps in specific embodiments when using optical lithography. The starting material can be a think magnesium foil, which can be covered on both sides with a thin layer of a positive photoresist by a spin coating technique followed by backing the resin. Next, the photoresist on both sides of the foil can be exposed to light with an appropriate wavelength through a photo mask which causes changes in the photoresist, making the exposed area soluble. This step can be followed by stripping off the soluble areas of the photoresist by an appropriate solvent thus creating a polymer mask directly attached to both sides of the magnesium foil. The following step can expose the magnesium foil to an etching solution which has access to the metal through the open areas of the masks from both sides. This step can cause complete etching out of the metal throughout the entire thickness of the foil. The etchant does not affect the photoresist masks which protects certain areas of magnesium and allows for creating the stent configuration. The final step is related to a lift off procedure that uses a solvent which removes only the remaining photoresist masks on both sides and liberated the etched foil.

In specific embodiments an additional procedure includes rolling the foil to form a cylinder or even a seamless cylinder. Two options are depicted. The first one leaves the formed cylinder "unlocked" (not sealed along the two longitudinal edges), which allows the stent to expand easily. The second approach details "locking" the etched magnesium cylinder along the side edges by ultrasonic spot welding, thus avoiding a requirement for any solder material. Laser spot welding is currently also conceivable. In specific embodiments, welding is performed with a magnesium electrode in an inert environment.

Figure 3B:
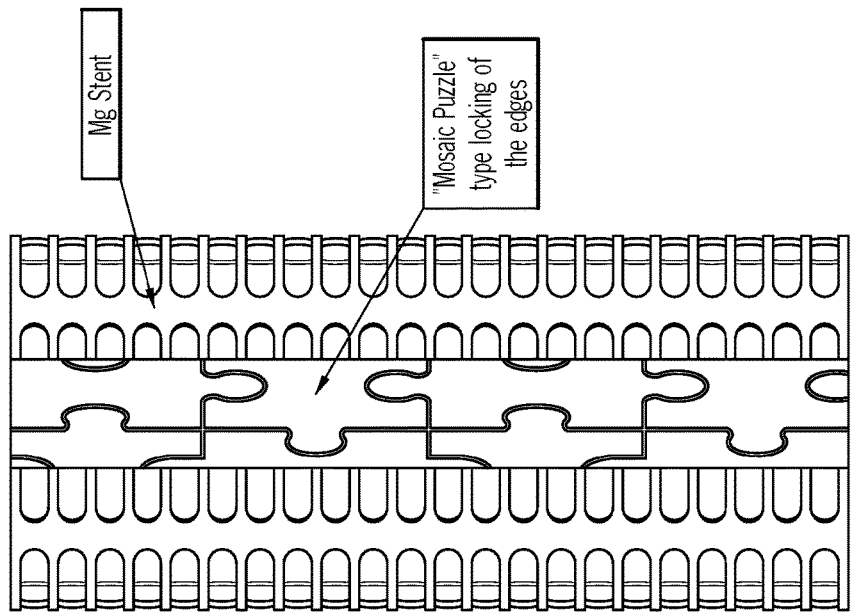
FIGS. 3a and 3b illustrate two non-limiting approaches for locking a stent cylinder along the side edges. 3a illustrates use of surgical suture or thin magnesium wire, while 3b illustrates a mosaic puzzle type locking of the edges.
Figure 3A:
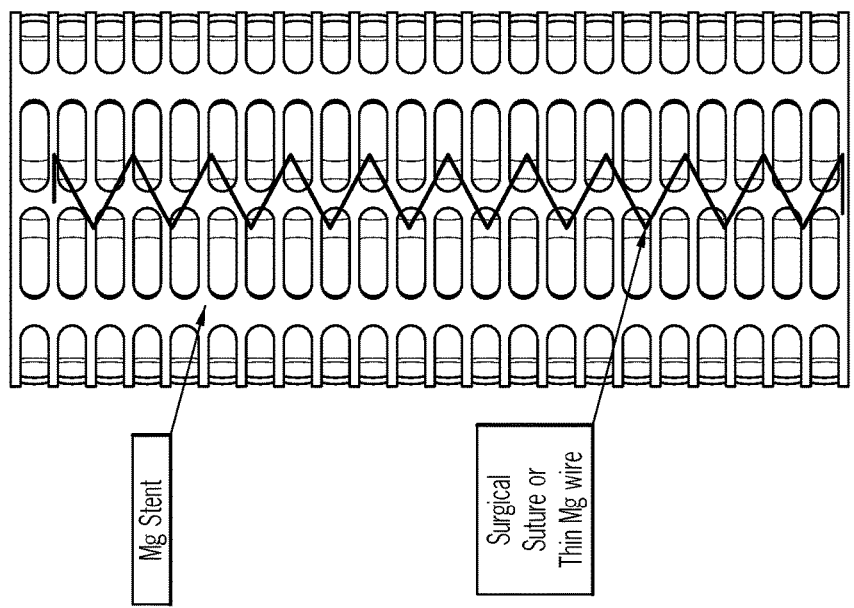

In specific embodiments another approach for "locking" the etched magnesium cylinder is by knitting both side edges with surgical suture or with thin magnesium wire along the length of the cylinder (see FIG. 3a). Another approach for "locking" the etched magnesium cylinder can be by snapping both side edges which are pre-shaped with an appropriate socket-stud (male-female) configuration as shown in FIG. 3b. This locking can resemble a "mosaic puzzle" type of coupling and the side edges can be shaped by a simple stamping operation.

Figure 4A:
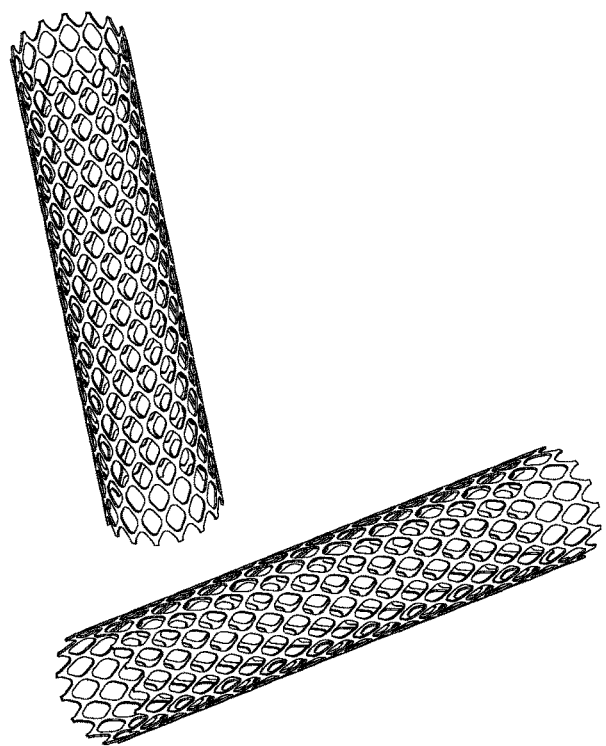
FIGS. 4a and 4b illustrate a magnesium stent manufactured through specific methods described herein, shown as a whole in 4a and enlarged in 4b.
Figure 4B:
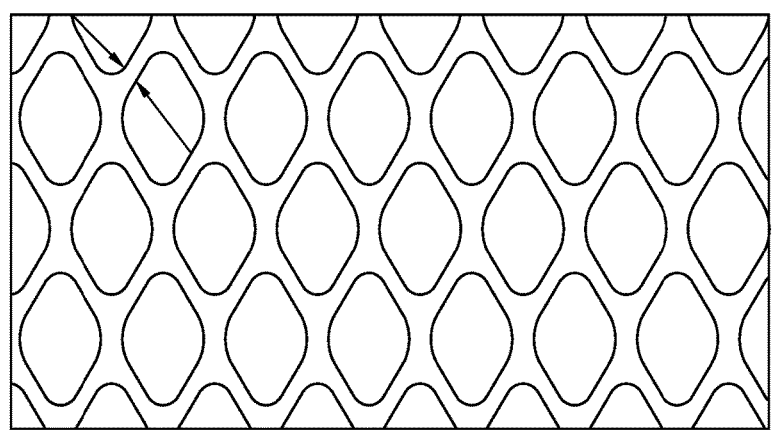

FIGS. 4a and 4b illustrate a magnesium stent manufactured through specific methods described herein, shown as a whole in 4a and enlarged in 4b.

Figure 5:
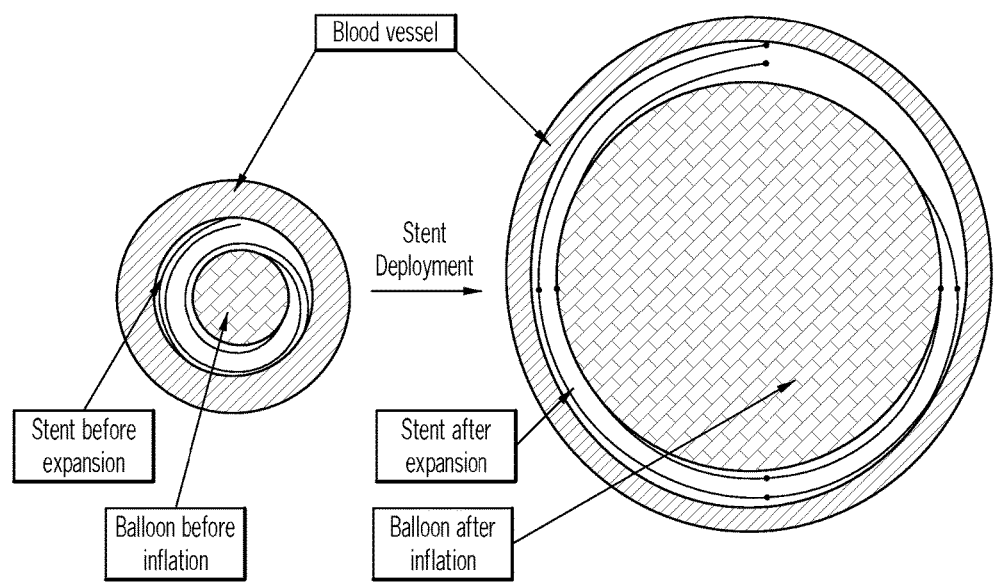
FIG. 5 illustrates a schematic of a balloon-expandable stent made by photochemical etching and in specific embodiments shaped into an unlocked cylinder which is folded to the point of overlapping the stent walls like a spiral.
Figure 6A:
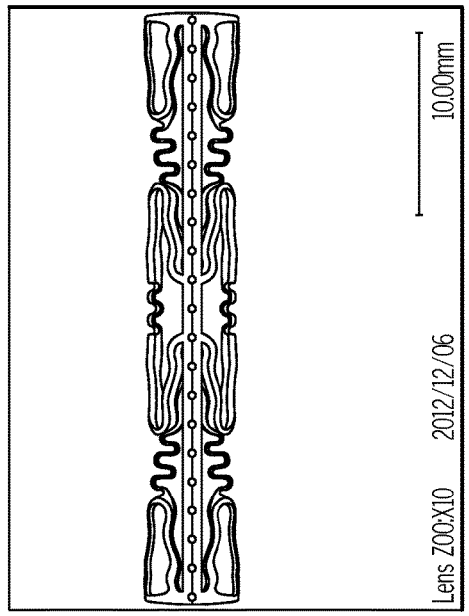
FIG. 6 illustrates non-expanded, laser welded magnesium stents. The bottom left panel (C) is an enlarged image of the top left panel (A), clearly showing the continuous weld of the stent. The bottom right panel (D) is an enlarged image of the top right panel (B), and shows an embodiment of a spot-welded stent.
Figure 6B:
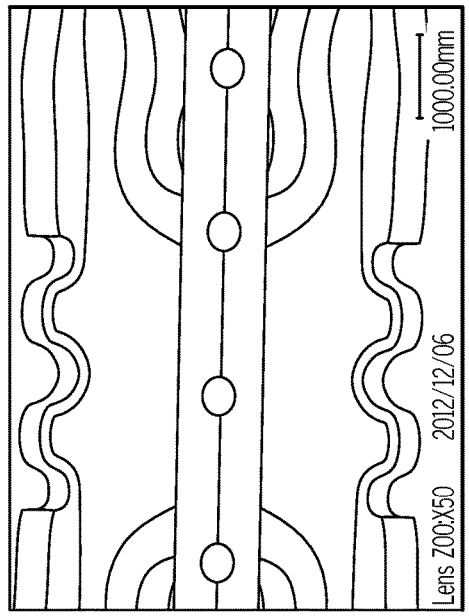
Figure 6C:
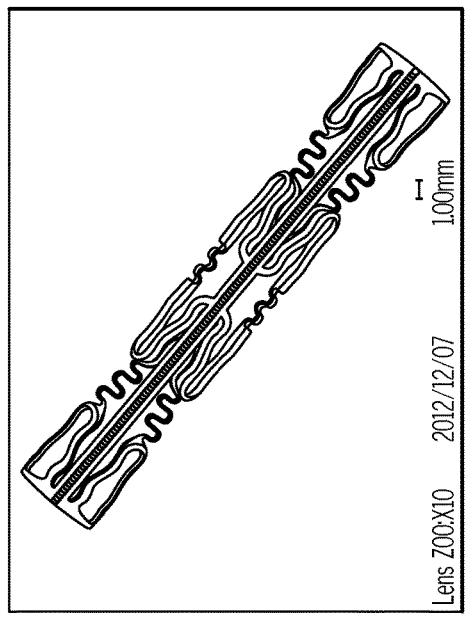
Figure 6D:
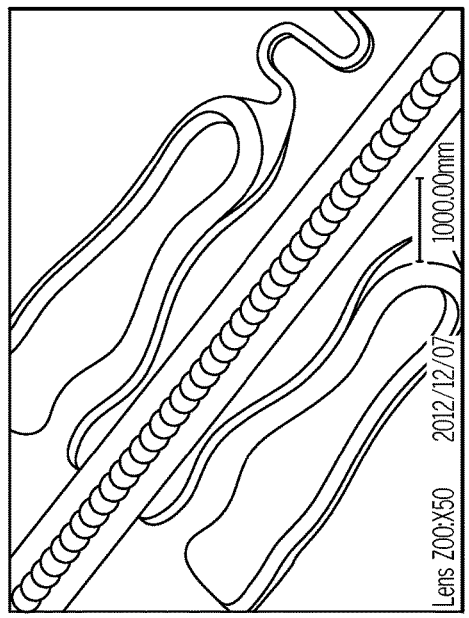

FIG. 5 illustrates a schematic of a balloon-expandable stent made by photochemical etching and in specific embodiments shaped into an unlocked cylinder which is folded to the point of overlapping the stent walls like a spiral. In specific embodiments, stents are designed by computer calculations for small, medium and large vessels, or small and large vessels, using data from libraries of information coupled to the computer for calculating stent design to determine optimal stent design for a vessel size.

FIG. 6 illustrates non-expanded, laser welded magnesium stents. The bottom left panel is an enlarged image of the top left panel, clearly showing the continuous weld of the stent. The bottom right panel is an enlarged image of the top right panel, and shows an embodiment of a spot-welded stent. Spot welding can include form one to dozens of spot-welds of varying thicknesses or equal thicknesses depending on the embodiment.

Figure 7:
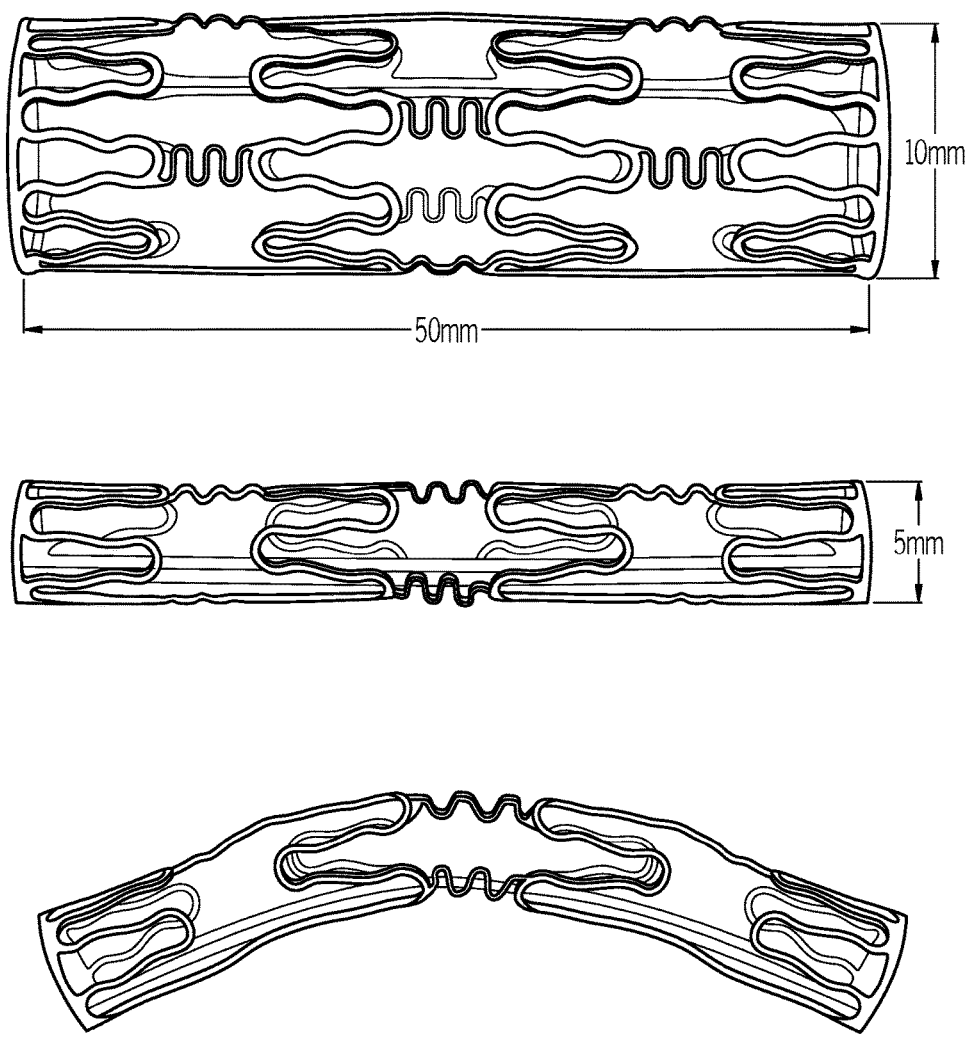
FIG. 7 illustrates various sizes and configurations of non-expanded stents showing a specific pattern and having an end ring at each end.

FIG. 7 illustrates various sizes and configurations of non-expanded stents showing a specific pattern and having an end ring at each end (along the cylinder longitudinal length of the rolled cylinder, which can be called top and bottom rings, when looking from left to right in the image, for example). In specific embodiments the ring or rings is of very thin diameter, in specific embodiments of thinner diameter than the diameter of the width of the weld holding together the longitudinal ends. In other embodiments there are form 1-4 rings at each longitudinal end of the stent, each of equal or varying thicknesses, with one or more of the rings being cut and/or removed to affect expansion rates. Expansion rates of the rings when cut and the center portions can be equal or unequal as needed by design. Additionally the stents can be from about 3 to about 30 micrometers in diameter prior to expansion and can be expandable from about 1 to about 4 times the original, non-expanded diameter. In specific embodiments the stent is about 50 millimeters in length, and in others, from 10 to 100 millimeters in length.

Figure 8A:
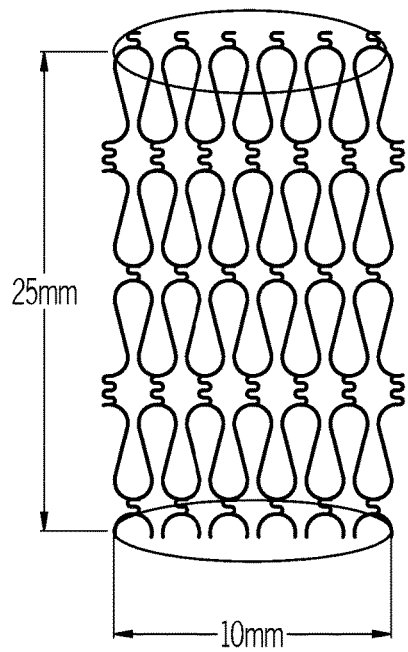
FIG. 8 illustrates drawings of specific embodiments (A-C) of stents described herein and indicates that the end rings are, in specific embodiments, removed prior to use and inflation of a balloon expanding or otherwise changing the configuration of the stent.
Figure 8B:
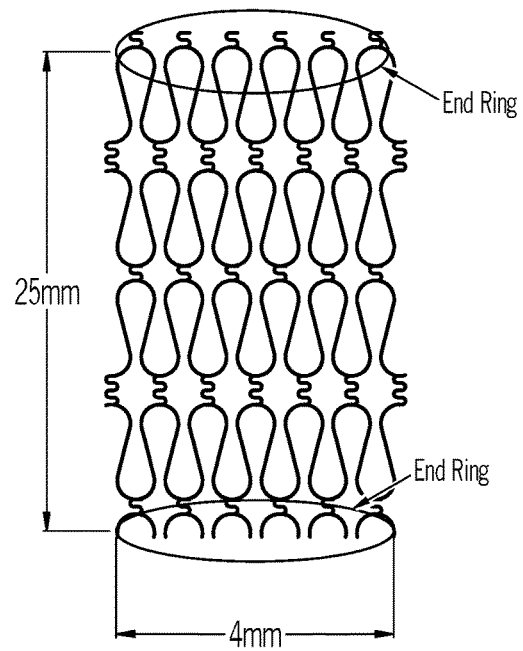
Figure 8C:
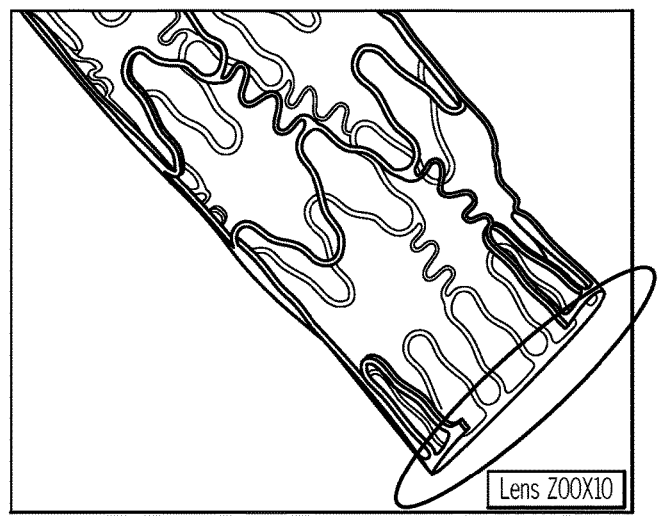

FIG. 8 illustrates drawings of specific embodiments of stents described herein and indicates that the end rings are, in specific embodiments, removed prior to use and/inflation of a balloon expanding or otherwise changing the configuration of the stent.

Figure 9A:
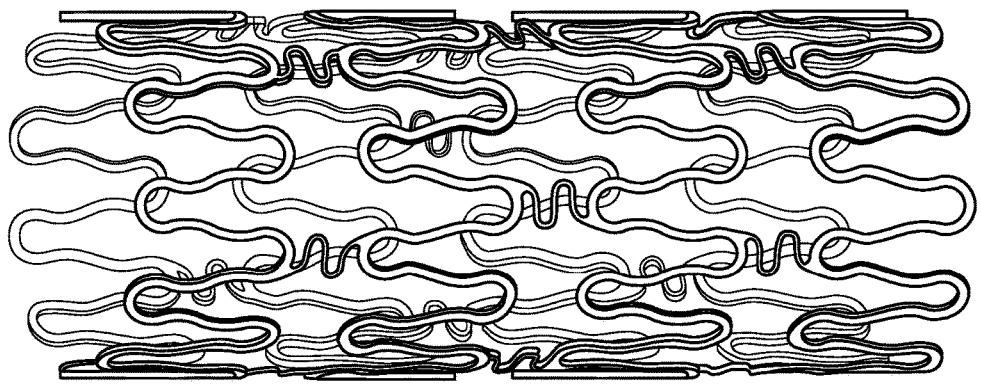
FIG. 9 illustrates additional drawings of specific embodiments of stents described herein (9a-9c).
Figure 9B:
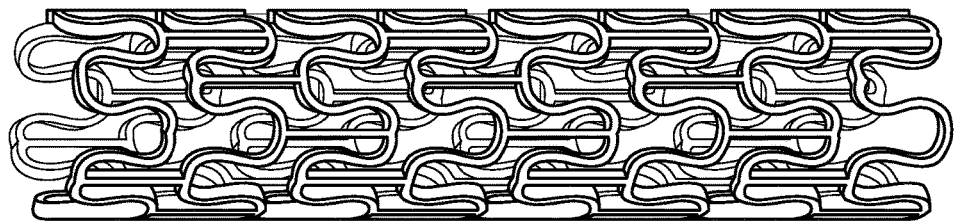
Figure 9C:
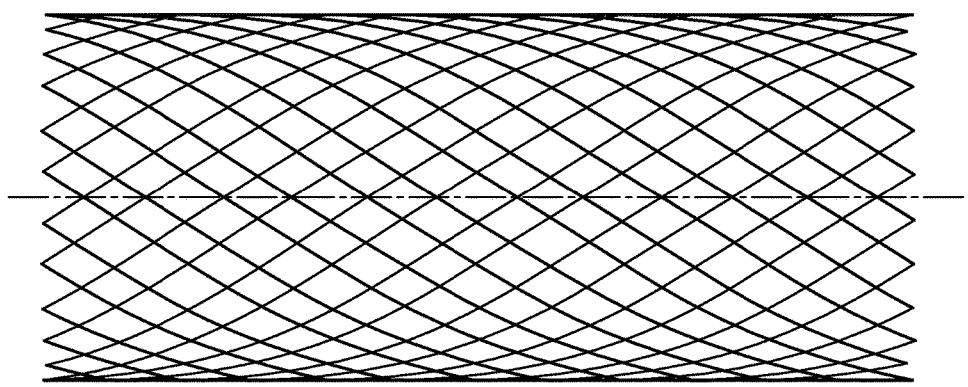

FIG. 9 illustrates additional drawings of specific embodiments of stents described herein (9a-9c).

Figure 10A:
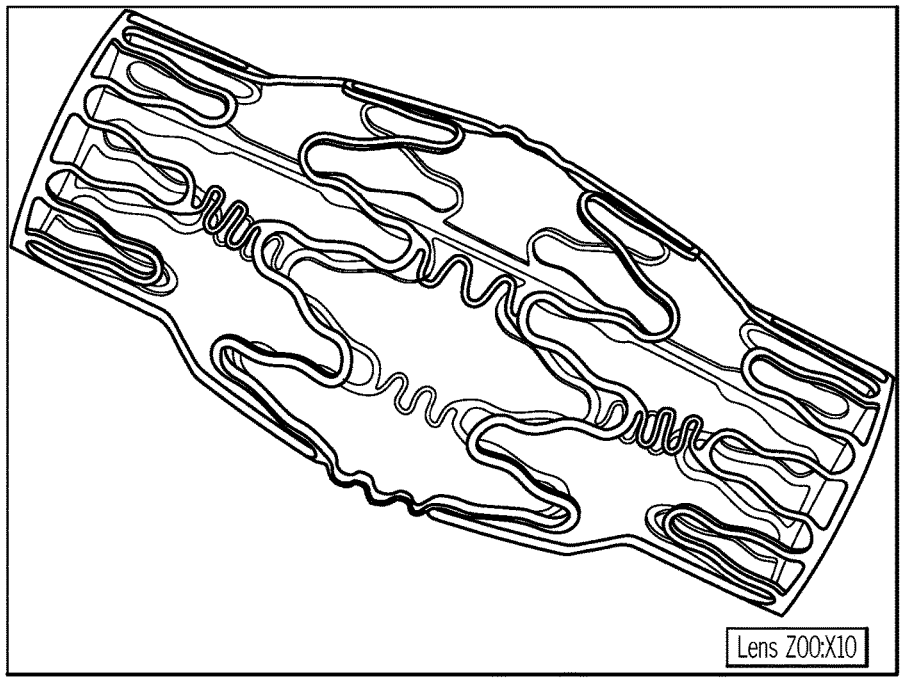
FIG. 10 illustrates a magnesium stent that has been expanded. The top panel (A) shows a stent expanded by a balloon at its center. The bottom panel (B) illustrates inflation of a balloon expanding one end of the stent.
Figure 10B:
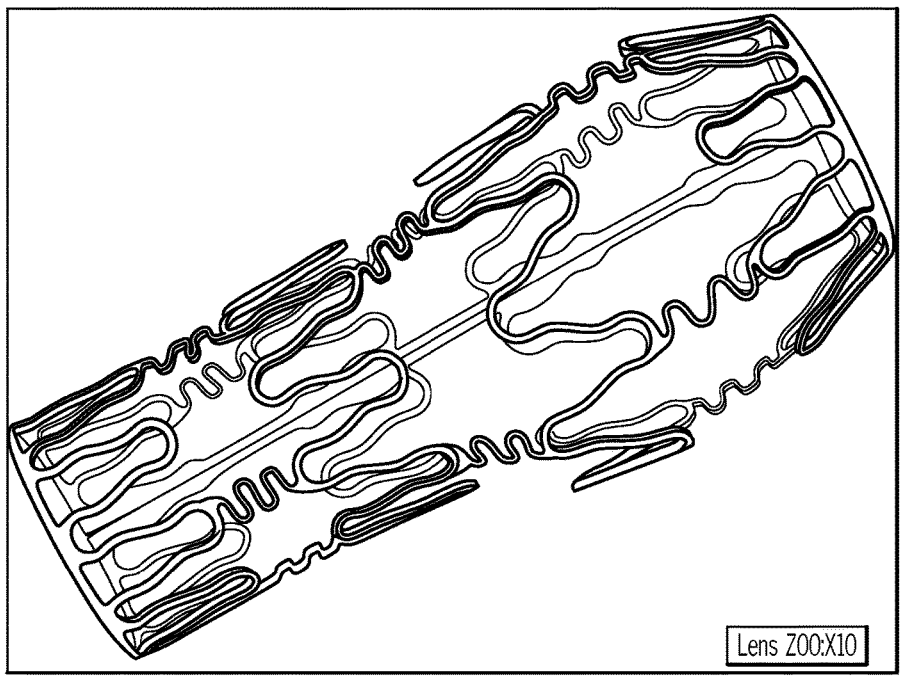

FIG. 10 illustrates a magnesium stent that has been expanded. The top panel show a stent expanded by a balloon at its center. The bottom panel illustrates inflation of a balloon expanding one end of the stent.

Figure 11:
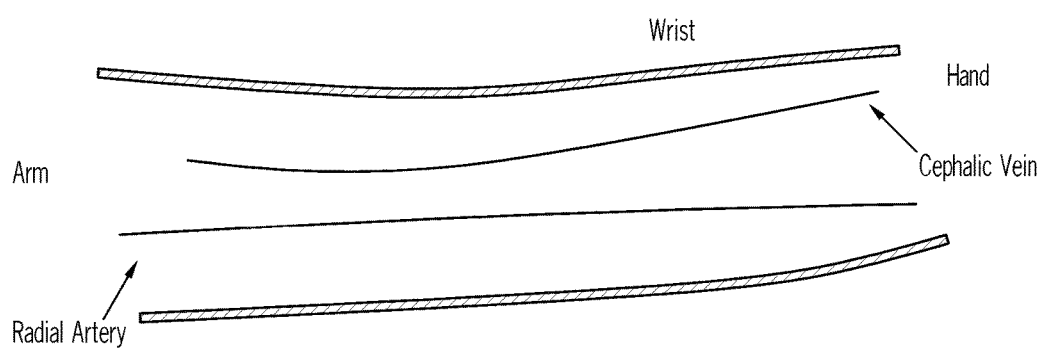
FIG. 11 illustrates a drawing of a human wrist indicating the cephalic vein and the radial artery.

FIG. 11 illustrates a drawing of a human wrist indicating the cephalic vein and the radial artery. This vein and artery can, in specific embodiments can be joined to create a surgically-created vascular access point via an arteriovenous fistulae (AVF). Other non-limiting examples include joining the cephalic vein and brachial artery, the basilic vein and brachial artery, the basilic vein and the ulnar artery, or creating an AVF below the antecubital fossa.

Figure 12:
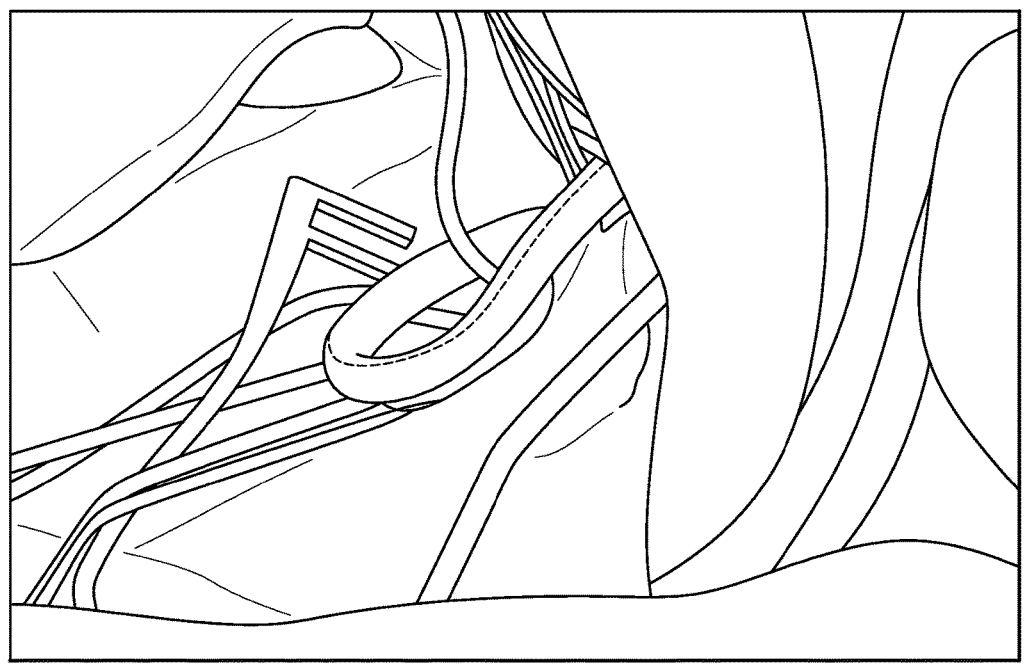
FIG. 12 illustrates a polytetrafluoroethylene (PTFE) graft.

FIG. 12 illustrates a PTFE graft Embodiments herein described provide alternatives to current graft technology and limitations.

Figure 13:
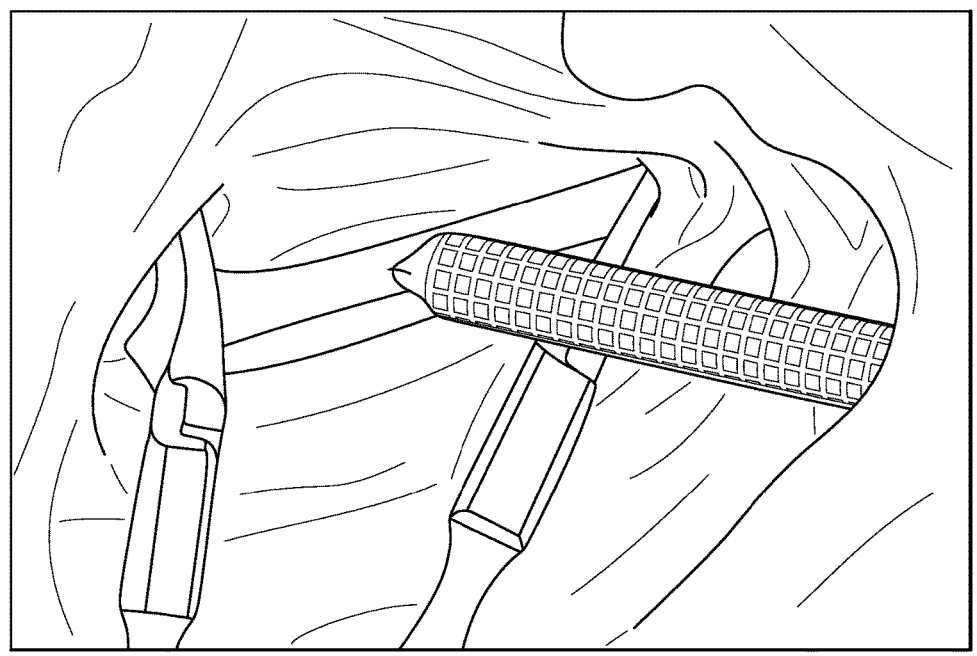
FIG. 13 illustrates stents can be placed, among other places, in specific embodiments in surgically created arteriovenous fistula formations as an alternative to a graft; the fistula can include various dimensions and angles to which the stent can be configured.

FIG. 13 illustrates a magnesium stent placed within a pig for stents that can be placed, among other places, in specific embodiments in surgically created arteriovenous fistula formations as an alternative to a graft. FIG. 13 shows use in a pig, though the stent can be used in other animals, including humans.

Figure 14A:
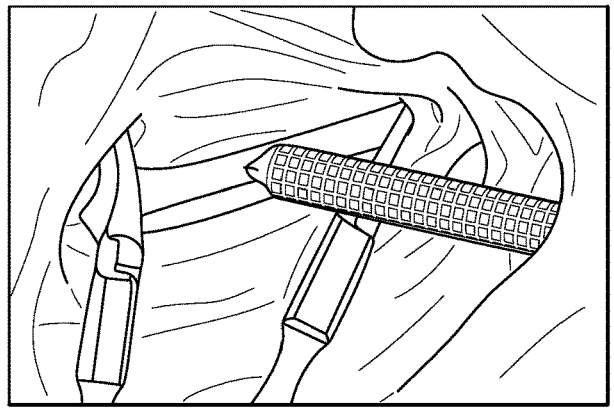
FIG. 14 illustrates, at FIG. 14a, a smaller version of the image shown in FIGS. 13, and at 14b and 14c, additional configurations of the stent are depicted.
Figure 14B:
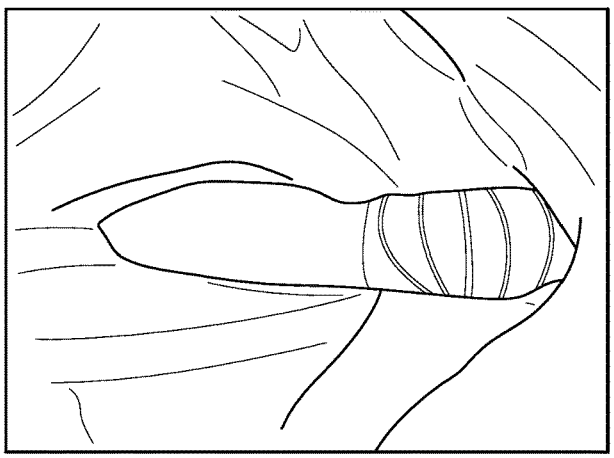
Figure 14C:
Figure 15A:
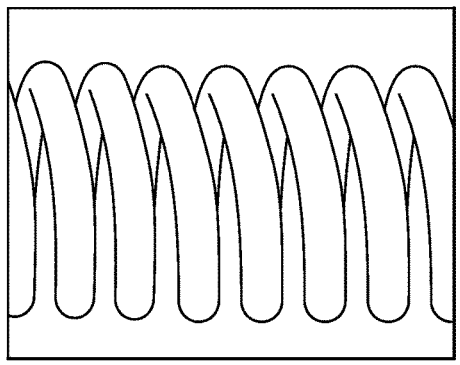
FIG. 15 illustrates different types, sizes, and configurations (A-D) of biodegradable maturation enhancing stents which in specific embodiments are placeable within a venous segment at the time of surgical ateriovenous fistula formation.
Figure 15B:
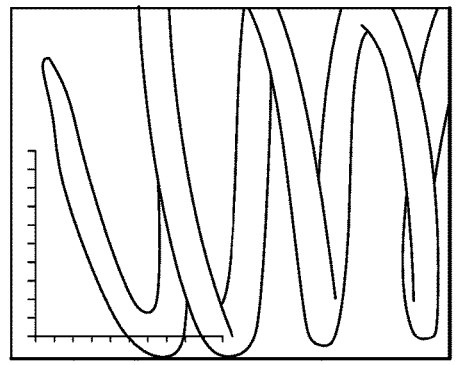
Figure 15C:
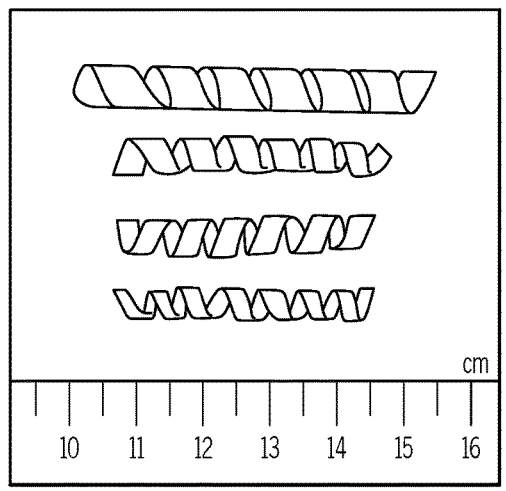
Figure 15D:
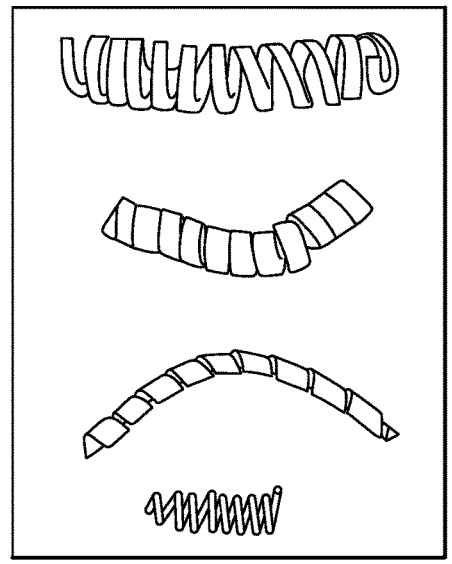

FIG. 14 illustrates, at FIG. 14a, a smaller version of the image shown in FIGS. 13, and at 14b and 14c, additional configurations of the stent are depicted.

FIG. 15 illustrates different types, sizes, and configurations of biodegradable maturation enhancing stents which in specific embodiments is placeable within a venous segment at the time of surgical arteriovenous fistula formation. The potential problem of failure can be potentially addressed by placement of a stent in a venous portion related to the stent. The stent can be wound into a coil or coil-like structure so that it can be configured at a necessary angle to promote maturation of a fistulae or to be used in other body portions and meet natural configurations of vessels, ureters, etc. Angles could be, in specific embodiments, from 30 to 120 degrees, for example.

Figure 16:
FIG. 16 illustrates stent delivery.

FIG. 16 illustrates stent delivery. The stents can be places in arteries or veins, or other sites in the body as necessary.

Figure 17A:
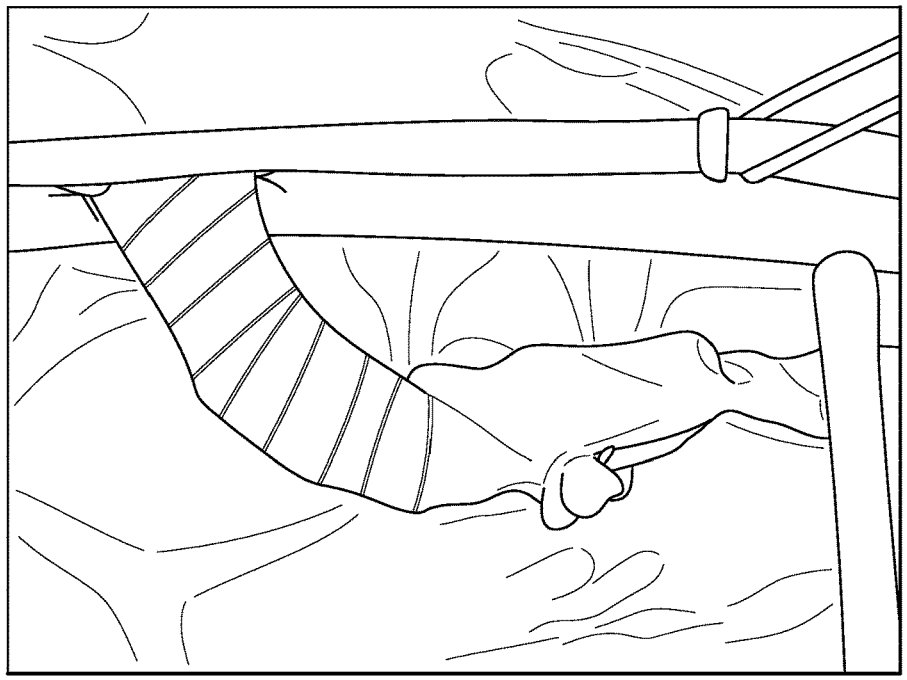
FIGS. 17a-17b illustrate two examples, specific configurations of placed stents as herein described.
Figure 17B:
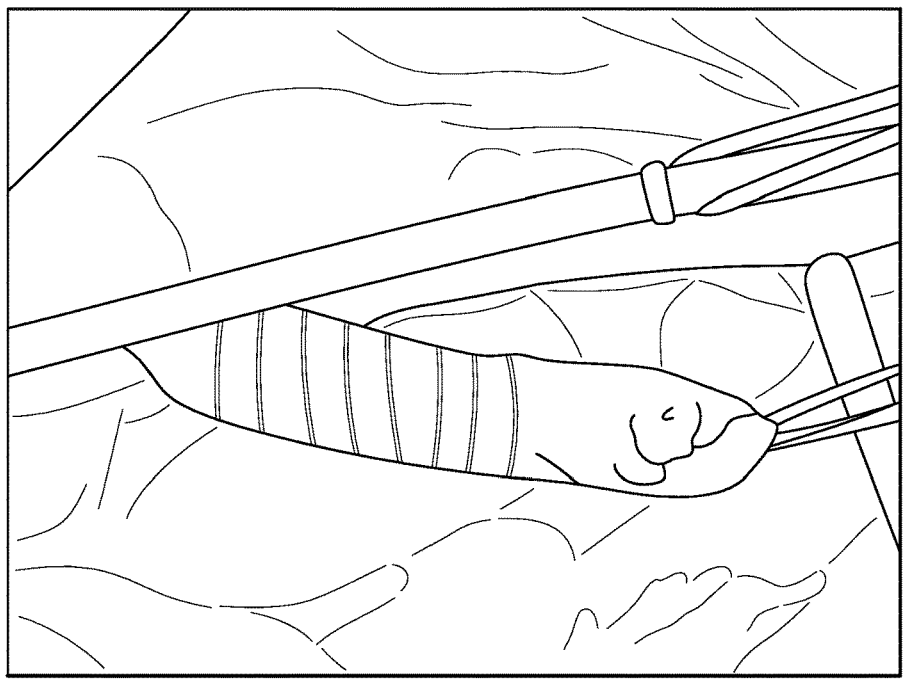
Figure 18A:
FIG. 18 illustrates specific embodiments (A-D) of additional placed stents.
Figure 18B:
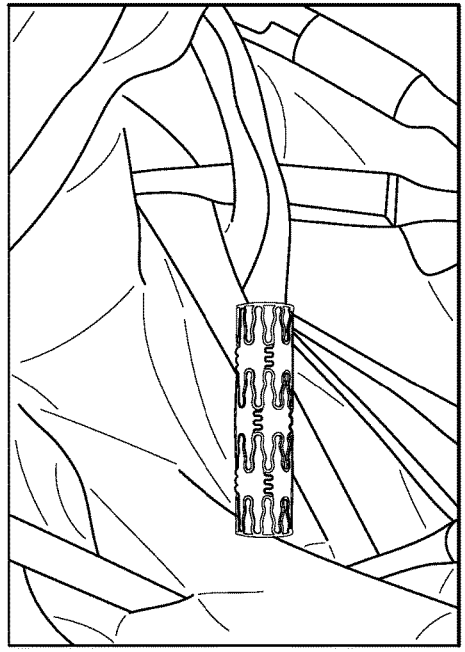
Figure 18C:
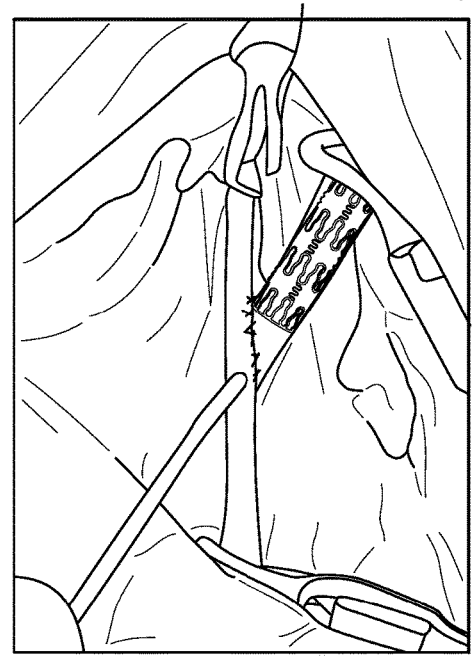
Figure 18D:
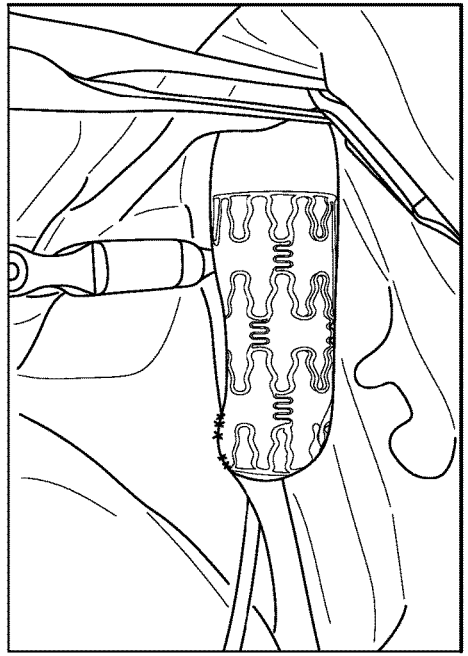

FIGS. 17a-17b illustrate two specific configurations of placed stents as herein described. The stents can be placed at various necessary configurations, including but not limited to including up to about one to about five angles each of from about zero to about one-hundred-twenty degree angles.

FIG. 18 illustrates additional, placed stents.

In specific embodiments the stent deployment can include balloon inflation. The stent can be wrapped like a spiral starting from the photo-etched magnesium foil and rolling it to an "unlocked" cylinder allowing folding it over several turns, which causes overlapping of the stent walls. Next, the non-inflated balloon can be inserted inside the cylindrical stent. After the stent is placed into the blood vessel using a conventional delivery technique, the balloon can be inflated and the stent can be unfolded, thus expanding to the walls of the blood vessel. This way the magnesium stent can be deployed without undergoing elastic deformation.

An advantage of specific, above-described approaches for manufacturing of the magnesium stents includes, but is not limited to, an avoidance of an expensive laser cutting operation. Specific, employed photochemical etchings are scalable processes that can take a short time, can be applied to foils with dimensions of 3 feet by 3 feet and greater, and do not require sophisticated facilities.

It should be understood that the present disclosure includes various aspects of embodiments.

In a first aspect, the magnesium based biodegradable stent for medical applications includes, but is not limited to, scaffolding of any blood vessels (cardiovascular, arteriovenous, fistula, etc.), urine ducts, bile ducts, and tracheal ducts.

In a second aspect, the disclosure provides a magnesium stent of the first aspect that can be made from magnesium foil with a composition including but not limited to pure magnesium, or magnesium alloys with any composition such as from the AZ series also non-doped or doped with rare earth elements (in non-limiting examples these can include light rare earth elements such as La, Ce, Pr, Nd, Pm, Sm, Eu, and Gd or heavy rare earth elements such as Tb, Dy, Ho, Er, Tm, Yb, Lu, and Y).

In a third aspect, the disclosure provides a magnesium stent of the first or second aspect wherein stent features and dimensions of the magnesium stent configurations can be made by using any lithographic techniques that can transfer the stent features to both sides of the magnesium foil followed by selective etching of magnesium.

In a fourth aspect, the disclosure provides for a magnesium stent of the third aspect, where the lithographic technique is Optical photolithography.

In a fifth aspect, the disclosure provides a magnesium stent of the third aspect, where the lithographic technique is electron beam lithography.

In a sixth aspect, the disclosure provides a magnesium stent of the third aspect, where the lithographic technique is x-ray lithography.

In a seventh aspect, the disclosure provides a magnesium stent of the third aspect, where the lithographic technique is Nanoimprint lithography.

In an eighth aspect, the disclosure provides a magnesium stent of the third aspect, where the lithographic technique is a combination of optical photolithography, electron beam lithography, x-ray lithography, and nanoimprint lithography, but is not limited to these lithographic techniques.

In a ninth aspect, the disclosure provides a magnesium stent of the third aspect, where the magnesium foil is processed by gas phase chemical etching from one or both sides.

In a tenth aspect, the disclosure provides a magnesium stent of the third aspect, where the magnesium foil is processed by wet chemical etching.

In an eleventh aspect, the disclosure provides a magnesium stent of the third aspect, where magnesium foil is processed by photochemical etching (etching enhanced by photons) wither in a gas or in a wet chemical etching environment.

In a twelfth aspect, the disclosure provides a magnesium stent of the third aspect, where the magnesium stent is provided by employing a procedure that includes rolling the etched magnesium foil to form a seamless cylinder.

In a thirteenth aspect, the disclosure provides a magnesium stent of the third aspect or the twelfth aspect, where the etched magnesium cylinder remains unlocked (not sealed along the side edges), which allow the stent to expand easily.

In a fourteenth aspect, the disclosure provides a magnesium stent of the third aspect or the twelfth aspect, where the etched magnesium cylinder is "locked" along the side edges by ultrasonic spot welding without using any solder material.

In a fifteenth aspect, the disclosure provides a magnesium stent of the third aspect or the twelfth aspect, where the etched magnesium cylinder is "locked" along the side edges by laser spot welding without using any solder materials.

In a sixteenth aspect, the disclosure provides a magnesium stent of the third aspect or the twelfth aspect, where the etched magnesium cylinder is "locked" along the side edges by welding with a magnesium electrode in an inert environment.

In a seventeenth aspect of the invention, the disclosure provides a magnesium stent of the third aspect or the twelfth aspect, where the etched magnesium cylinder is "locked" along the side edges by knitting both edges with a surgical suture.

In an eighteenth aspect, the disclosure provides a magnesium stent of the third aspect or the twelfth aspect, where the etched magnesium cylinder is locked along the side edges by knitting both edges with a magnesium wire.

In a nineteenth aspect of the invention, the disclosure provides a magnesium stent of the third aspect or the twelfth aspect, where the etched magnesium cylinder is "locked" along the side edges by coupling/snapping both edges.

In a twentieth aspect, the disclosure provides a magnesium stent of the third aspect, the twelfth aspect, or the nineteenth aspect, where both side edges are shaped with an appropriate socket-stud (male-female) configuration.

In a twenty-first aspect, the disclosure provides a magnesium stent of the third aspect or the thirteenth aspect, where the magnesium stent is balloon-expandable and where the unlocked cylinder is folded to the point of overlapping the stent walls like a spiral, which enables the deployment of the stent.

In aspects of specific embodiments herein: gas phase chemical etching is used, wet chemical etching is used, cylinders can be cylinder balloon-expandable, be left unlocked such that there is a longitudinal gap between the two edges along a longitudinal length of the cylinder, be configured such that the cylinder's two edges along the longitudinal length overlap each other such that a spiral is formed as seen from a side view looking down the longitudinal length of the stent. In more specific embodiments, the cylinder can be locked along the longitudinal edges by knitting both edges with either a surgical suture, a magnesium wire, or a snap, or by a mosaic puzzle configuration comprising two or more interlocking male-female connections, and configuring the cylinder to have the two or more interlocking male-female connections oriented at different angles with respect to the longitudinal length of the cylinder. In more specific embodiments, laser welding can be performed on at least a portion of the side of the magnesium cylinder, the stent can have upper or lower rings or both (the rings being at each end along the longitudinal length of the cylinder respectively), and the rings can be removed by etching, mechanical cutting, or laser cutting after the step of laser welding. In more specific embodiments, after ring removal additional etching can be performed, or the rings can be left in place and cut through partially or fully and any angle so as to be discontinuous. In specific embodiments, as to the rings, methods comprising removing all longitudinal sections of a welded seam between all circumferential struts on the stent, such that the stent is stress-free with regards to longitudinal contraction of the stent and such that bending of the stent is prevented and overstressing or breaking of meandering wire connections between the struts is also prevented when the stent is expanded. In specific embodiments post-surgery a functionality of a vessel of the surgery can be assessed using doppler or other devices for measuring blood flow or visualizing blood flow. Specific embodiments involve the carotid artery and a jugular vein, and coating a stent with one or more of angiotensin-converting-enzyme inhibitor, a nonselective phosphodiesterase inhibitor, calcium channel blockers, a platelet inhibitor, or fish oil prior to the step of inserting the stent into the vein. Specific embodiments herein involve inserting the stent into the vein (or an artery) endovascularly and/or wherein the endovascular insertion is additionally performed across an anastomosis and further comprising dilating the vein endovascularly, and/or inserting a dilatation device through the vein to dilate the entire stent. In other embodiments there is manipulation of a configuration of the stent after dilatation in order to optimize flow within the vessel, and/or the surgical area is covered, and/or the method involves completing an anastomosis of a vein and an artery. In yet more specific embodiments, a stent is placed in an artery and a vein during the same surgery, and/or in others the method involves designing the stent to allow for blood flow changes into the vein as a result of an anastomosis of the vein and the artery and to allow for any changes in vein structure and size that occur post-surgery (the design can account for optimization to either change or otherwise increase functionality or maximize blood flow through an area). In other embodiments the stent can be covered in full or in part by a sleeve and more than one sleeve can be used in a given surgery for one or more veins or arteries or both. In yet more specific embodiments the stent could be placed through laparoscopy.

EXAMPLES

The described embodiments will be better understood by reference to the following examples, which are offered by way of illustration and which one skilled in the art will recognize are not meant to be limiting.

Example 1

Method of Making a Magnesium Biodegradable Stent for Medical Implantations Using Photochemical Etching Steps for making the biodegradable stent using photochemical etching includes, in specific embodiments, making a mask by designing features and their dimensions using computer software. The mask can be transferred on a transparent foil or glass plate by printing or by photo process. Cleaning the Mg foil can be performed using solutions. The foil can then be laminated a photosensitive polymer such as polymer 4. The photosensitive polymer can be exposed to ultraviolet light through the mask (and this can be done for one or both sides of the foil). The polymer exposed to the mask becomes soluble. This step 4 is done on both sides of the laminated Mg foil. The soluble portion of the polymer can be removed, opening windows having the stent features on the polymer surface on both sides of the laminated magnesium foil. The laminated foil can be etched on both sides by dipping in a magnesium etchant such as HCL or HNO$_3$ acid, or by using nozzles to spray the HCL or HNO$_3$ on both sides. The laminated foil can be rinsed, and the residual polymer can be removed by dipping in a solvent for the polymer thus liberating the etched magnesium foil. The magnesium foil can then be rinsed and segments can be cut from the etched magnesium foil. In specific embodiments the magnesium foil can be rolled to shape into a cylinder, and can be laser welded of the side of the magnesium cylinder.

In specific embodiments the cylinder is designed such that an upper and lower ring is present at the sides of the foil along the longitudinal length of the cylinder. This provides a surprising amount of support during the rolling process. In specific embodiments the rings are solid segments of aluminum or aluminum alloy, and in other segments they are of continuous lengths that may or may not have partial etchings along the length. In an additional step, the upper and/or lower rings of the etched magnesium cylinder can be removed by etching and/or mechanical and/or laser cutting. This can be performed as the solid rings and the rest of the stent generally do not have the same properties, so upon balloon expansion the sections do not expand in the same way to the same rate or the same extent. Electro-polishing of the magnesium etched stent can then be performed. In specific embodiments the magnesium stent design has a single, continuous longitudinal weld along the longitudinal length that is of greater width than the width of either of the end rings.

Example 2

Use of Magnesium Biodegradable Stent for Enhancing Arteriovenous Fistula

The value of safe, effective methods and devices for performing hemodialysis cannot be underestimated. The Center for Disease Control (CDC) reported in 2012 that in the United States alone, there were about 370,000 people relying on hemodialysis care. Depending on the functioning level of one or both kidneys, a patient may require hemodialysis as a life saving measure, as the blood is passed through a dialyzer to filter out particles and toxins. However such measures can be intrusive and time consuming, in specific cases taking up to three to five hours and having to be performed three times a week.

To ensure adequate and reliable entry points are available to a patient's vasculature system, three main techniques are currently employed. Current main types of access include catheter, arteriovenous (AV) graft and arteriovenous (AV) fistula. However there are various drawbacks to each technique.

According to the CDC, About 75,000 people receive hemodialysis through a central line (central venous catheter). Central lines have a higher risk of infection than a graft or fistula. The CDC estimates that 37,000 central line-associated bloodstream infections may have occurred in U.S. hemodialysis patients in 2008. Catheters also sometimes require cuffs for stabilization, have a lower flow rate than other options, and simply can preclude various activities (swimming or bathing, etc).

Grafts are created by connecting a vein to an artery using a connective device that in many cases is a soft plastic tube. After the graft has healed, hemodialysis is performed by placing two needles; one in the arterial side and one in the venous side of the graft. The graft allows for increased blood flow since there is a connection between the arterial system and the low resistance venous system. However grafts tend to need attention and upkeep due to thrombosis and stenosis.

Arteriovenous fistulae (AVFs) are the preferred mode of permanent dialysis vascular access because of better long term survival and reduced infection risk as compared to dialysis grafts and catheters. This has resulted in a federal initiative to increase AVF prevalence, called "Fistula First." Unfortunately, recent large studies have documented that only 40% of AVFs are suitable for hemodialysis at 4-5 months post surgery, with most AVFs failing to mature because of a peri-anastomotic venous segment stenosis. This is thought to be due to aggressive neointimal hyperplasia (NH) compounded by a failure of venous dilation. At a pathogenetic level the three main causes for AVF maturation failure are (a) small veins that are unable to undergo adequate dilation in response to increased flow (b) an abnormal hemodynamic profile which predisposes to both NH and a lack of outward remodeling (dilation) (c) abnormal local endothelial function as a result of oxidative stress and inflammation in uremic patients, resulting in a predisposition to NH and impaired outward remodeling.

Specific embodiments herein describe comprise placement of a biodegradable maturation enhancing stent (hMES) within the venous segment to provide significant enhancement of arteriovenous (AVF) maturation. In specific embodiments the stent can be placed in a venous segment at the time of the surgical creation of the AVF. A vein, for example, that is about 2 millimeters in diameter may have a typical flow rate of 30-50 milliliters per minute. The stent can, in specific embodiments, can be inserted and in specific cases expanded so as to increase to about 4 millimeters or more in diameter. In specific embodiments a vein size can be increased from about 1 to about 4 fold by the stent, and flow rate can increase from about one to about thirty fold after creation of an AVF For example, the flow rate of 30-50 milliliters per minute, described previously, could be increased to 500-1000 milliliters per minute following creation of an AVF with the placement of the stent as opposed to poor flow and thrombosis if the AVF is created without the stent. In specific embodiments, any of the stents herein described can be provided, and the methods for medical application can include surgically creating an AVF, inserting a biodegradable stent as described herein, and placing the stent within a venous segment of the AVF at the time of surgical creation.

In specific embodiments a malleable, coated (drug/gene/cell/chemical maturation enhancing stent (bMES), or any stent described herein, is placed within the venous segment or even extending into the proximal arterial segment at the time of surgical AVF creation to have the following effects: (a) keep open small veins during the critical first months and more importantly cause an instantaneous dilation of these small veins and also arteries so that the chance of developing a high blood flow immediately after surgery is increased greatly and this same high blood flow (ideally in a smooth laminar format) could then allow for better outward dilatation of the AVF and also prevent neointimal hyperplasia (h) allow the surgeon to optimize the anatomical (surgical) configuration with a malleable stent, resulting in laminar flow and decreasing shear stress in areas of the surgery and outflow vein thus increasing "good" shear stress profiles, the "good" profiles being aspects that increase the chance of AVF maturation and which could be computer modeled prior to placement. The "good" profiles would lead to inhibition of neointimal hyperplasia and enhance outward remodeling (c) the physical structure of the bMES could be used as a conduit for the delivery of drugs, cells, genes or chemicals that could counter the abnormal vascular biology. In specific embodiments the bMES or any other stent herein described can be coated with ACE-I, PENTOXIPHYLLINE, calcium channel blockers, DIPYRIDAMOLE, or fish oil. Factors can be applied in specific embodiments to block smooth muscle cell/fibroblast/myofibroblast migration and proliferation. Other coatings could have anti-oxidant and anti-inflammatory coatings (d) the stent scaffold with its coatings could protect the area of surgical injury and vein handling against aggressive neointimal hyperplasia and inward collapse and/or constriction; the coatings could also alter the local biological milieu and counteract the effects of uremia, oxidative stress and inflammation (e) the open configuration of the stent along its longitudinal aspect could allow for ongoing dilatation over and above its initial dilatation.

Embodiments herein can be used to optimize the hemodynamics increase thermodynamics of a vessel, ureter, etc. Differing techniques can be used to determine the ideal configuration which would allow for optimal shear stress profiles. Flow rates before and after implantation can be determined to provide or be used in an estimation of effectiveness of the stent placement.

Stents herein can be designed to include coatings on the interior or exterior or both to decrease neointimal formation or to increase vessel diameter (such as nitric oxide for dilation, PACLITAXEL or SIROLIMUS or other anti-proliferative and anti-inflammatory agents, or immune suppressants or mitotic inhibitors); for all embodiments herein described, generic versions of described coatings can also be used. Combinations of coatings are also conceivable.

Specific embodiments herein described significantly improve upon current methods of stent manufacturing and degradation. Specific embodiments of the stents herein described degrade reliably within 3 months. Complete degradation can be designed to occur, for example, from about 1 to about 3 months. Computer calculations can also be used to determine, based on vessel size, the parameters of stent design, production, and configuration.

In specific embodiments herein described, venous segment diameters and volume blood flow (duplex ultrasound), and also the magnitude of NH from previous experiments in animals and/or data from implementation in humans can be used to determine the parameters of stent production.

In specific embodiments herein described, the biodegradable stents can be utilized not only enhance AVF maturation rates but also to allow for the surgical creation of AVFs in patients who would currently not be AVF candidates, due to small vessels or multiple cardiovascular co-morbidities. In particular, the biodegradable stent technology could allow for an increased placement of AVFs in pediatric populations, where currently over 50% of permanent hemodialysis vascular access is through the use of tunneled dialysis catheters, with their attendant problems of infection and thrombosis. The stents could be used in conjunction with other surgical procedures such as grafts.

In specific embodiments stents can be placed in animals, including humans. In specific non-limiting embodiments regarding placement, steps are as follows: animals are anesthetized, surgically prepped, and given pre-emptive analgesics; incisions are made as appropriate for the subsequent AVN placement; an AV fistulae is created with an end to side anastomosis between the carotid artery and jugular vein (internal jugular or external jugular) in the neck in different configurations and sizes or between the femoral artery and vein or between any other artery and vein in close proximity and which is relatively superficial; creating an arteriovenous fistulae with an end to side anastomosis between an artery and a vein; inserting the stent into the vein using a sleeve over the stent as needed and crimping the stent as needed; positioning the stent so a first end of the stent is aligned with an open end of the dissected vein; suturing the vein to the artery; incising the artery across the anastomosis; inserting a balloon via the incision in the artery to the stent; expanding the balloon to expand the stent; and suturing the incision in the artery; or alternatively placing the stent under direct vision into the cut end of the vein with or without a sleeve and/or crimping device, performing the anastomosis and then dilating the stent through a venous approach. Alternatively, the stent can be configured so that it extends into the artery as needed and covers the entire peri-anastomotic area; with the stent being configured/designed such that arterial flow comes in well through the gaps in the stent. The stent could also be configured into different anatomical configurations before or after placement in order to optimize blood flow. Application and placement into additional sites of the vasculature, including venous segments of different veins are conceivable.

In specific embodiments, when the stent is expanded radially it will tend to shorten axially in length. However, the longitudinal welded seam needed to close the stent will not change length thus causing the stent to bend under radial expansion. Also, the small meandering wires interconnecting the struts will become overstressed near the longitudinal seam. To avoid this problem, in specific embodiments the longitudinal sections of the welded seam should be removed between all of the circumferential struts on the stent. Removing the longitudinal seam except at the struts will allow stress-free longitudinal contraction of the stent and prevent bending of the stent and overstressing or breaking the meandering wire connections between the struts when the stent is expanded. Other engineering advances will allow for the stent shape to be changed to optimize hemodynamics and laminar flow and for there to be a longitudinal open seam to allow for self expansion if the vein continues to enlarge more than the initial expanded stent diameter.

The stents could be used at all points within the dialysis access circuit including the arterial inflow, the arteriovenous anastomosis for an AVF or the artery-graft and graft-vein anastomoses for an AV graft, the outflow vein, the large more proximal veins and the central veins.

An important feature/strength is the biodegradable nature which allows for the stent to exert its multiple beneficial effects (increase the size of the vessels, optimize configuration and hemodynamics allow for the release of agents which optimize the biological milieu) in the first 1-6 months after AVF creation but which then also prevents the long term problems of having a foreign body in the circulation long term which includes the risks of stenosis and thrombosis and the long term need of expensive anti-clotting agents which themselves have a risk profile.

The invention claimed is:
1. A method for making a magnesium biodegradable stent for medical implant applications comprising:
   providing a magnesium foil comprising pure magnesium or magnesium alloys that are biodegradable;
   performing a lithographic technique to configure and transfer features of the stent to both sides of the magnesium foil, wherein the lithographic technique is selected from at least one of optical photolithography, electron beam lithography, x-ray lithography, and nanoimprint lithography, or a combination of these techniques;

etching the magnesium foil by wet chemical etching or gas phase chemical etching;

rolling the magnesium foil to form a cylinder comprising a longitudinal length, two longitudinal edges, a side, and a circular cross-section having a diameter, at least two features of the cylinder comprising an upper ring and a lower ring, the rings located at each end of the longitudinal length of the cylinder;

laser welding at least a portion of the side of the magnesium cylinder; and removing the upper and lower rings of the cylinder by etching, mechanical cutting, or laser cutting after laser welding.

2. The method of claim 1 wherein the etching of the magnesium foil comprises gas phase chemical etching.

3. The method of claim 1 further comprising configuring the cylinder such that the cylinder is balloon-expandable, and leaving the cylinder left unlocked such that there is a longitudinal gap between the longitudinal edges along the longitudinal length of the cylinder.

4. The method of claim 1 further comprising configuring the cylinder to be locked along the longitudinal edges by knitting both edges with either a surgical suture, a magnesium wire, or a snap.

5. The method of claim 1 further comprising configuring the cylinder to be locked along the longitudinal edges by a mosaic puzzle configuration comprising two or more interlocking male-female connections oriented at different angles with respect to the longitudinal length of the cylinder.

6. The method of claim 1 further comprising cutting the upper and lower rings completely through at two or more sites with an approximately cross-sectional cut approximately parallel with the longitudinal length of the stent such that the rings are discontinuous.

7. The method of claim 6 further comprising removing all longitudinal sections of a welded seam between all circumferential struts on the stent, such that the stent is stress-free with regards to longitudinal contraction of the stent and such that bending of the stent is prevented and overstressing or breaking of meandering wire connections between the struts is also prevented when the stent is expanded.

8. The method of claim 1 further comprising cutting the rings every 30 or 45 degrees around each ring.

9. The method of claim 8 further comprising configuring the cylinder to be balloon expandable to at least two times the diameter of the stent prior to expansion.

10. The method of claim 9 additionally comprising the step of lining an interior surface of the cylinder with a gel foam wrap configured to be pre-loaded with a releasable chemical.

11. The method of claim 1, wherein removing the upper and lower rings is performed by etching.

12. The method of claim 11 wherein removing the upper and lower rings is performed such that after the etching, each end of the stent comprises a series of rounded loops.

13. The method of claim 11, further comprising removing material from each end of the stent by etching, mechanical cutting, or laser cutting after removing the upper and lower rings.

* * * * *